United States Patent
Ouchi

(10) Patent No.: US 6,245,078 B1
(45) Date of Patent: Jun. 12, 2001

(54) SNARE FOR ENDOSCOPE

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/453,897

(22) Filed: Mar. 27, 2000

(30) Foreign Application Priority Data

Apr. 26, 1999 (JP) .................................. 11-117415

(51) Int. Cl.[7] .................................. A61B 17/22
(52) U.S. Cl. .................................. 606/113; 606/114
(58) Field of Search .................................. 606/113, 114, 606/110

(56) References Cited

U.S. PATENT DOCUMENTS

| | | | |
|---|---|---|---|
| 3,739,784 | * | 6/1973 | Itoh ........................ 606/113 |
| 3,828,790 | * | 8/1974 | Curtiss et al. ............ 606/113 |
| 4,643,187 | | 2/1987 | Okada . |
| 5,084,054 | * | 1/1992 | Bencini et al. .......... 606/113 |
| 5,108,406 | * | 4/1992 | Lee ........................ 606/206 |
| 5,201,740 | * | 4/1993 | Nakao et al. ............ 606/113 |
| 5,201,741 | * | 4/1993 | Dulebohn ................ 606/113 |
| 5,281,238 | * | 1/1994 | Chin et al. ............... 606/113 |
| 5,417,697 | * | 5/1995 | Wilk et al. ............... 606/113 |
| 5,746,747 | * | 5/1998 | McKeating ............... 606/113 |
| 6,036,698 | * | 3/2000 | Fawzi et al. ............. 606/114 |
| 6,068,603 | * | 5/2000 | Suzuki ..................... 606/113 |

FOREIGN PATENT DOCUMENTS 6-3549   2/1994   (JP) .

* cited by examiner

*Primary Examiner*—Paul J. Hirsch
(74) *Attorney, Agent, or Firm*—Greenblum & Bernstein, P.L.C.

(57) ABSTRACT

A snare for an endoscope has a snare wire formed from an elastic wire that is connected to the distal end of a control wire axially movably inserted in a flexible sheath. When the control wire is advanced axially, the snare wire projects from the distal end of the flexible sheath and expands in a loop shape by its own elasticity. When the control wire is retracted axially, the snare wire is pulled into the distal end of the flexible sheath and thus contracted. The distal end surface of the flexible sheath is provided with a plurality of claw-shaped projections projecting forward in parallel to each other.

6 Claims, 4 Drawing Sheets

SNARE FOR ENDOSCOPE

REFERENCED-APPLICATIONS

The present disclosure relates to subject matter contained in Japanese Patent Application No. 11-117415 (filed on Apr. 26, 1999), which is expressly incorporated herein by reference in its entirety.

STATEMENT REGARDING FEDERALLY SPONSORED RESEARCH

Not Applicable

REFERENCE TO A MICROFICHE APPENDIX

Not Applicable

BACKGROUND OF THE INVENTION

1. Description of Prior Art

In general, a snare for use with an endoscope has a snare wire formed from an elastic wire that is connected to the distal end of a control wire axially movably inserted in a flexible sheath. The snare wire projects from or withdraws into the distal end of the flexible sheath in response to an operation of advancing or retracting the control wire in the axial direction. When projecting from the distal end of the flexible sheath, the snare wire expands in a loop shape by its own elasticity. When pulled into the distal end of the flexible sheath, the snare wire contracts.

However, the snare having the above-described simple structure suffers from a problem arising when a stemless polyp or the like is to be bound tight with the snare wire. That is, when a stemless polyp is encircled with the snare wire expanded in a loop shape and the snare wire is contracted by pulling the control wire, the snare wire may slip on the surface of the polyp and fail to pinch it.

Accordingly, the conventional practice is to secure a plurality of anti-slip tips to the snare wire so that the anti-slip tips project from the inner surface of the loop to bite into the polyp when the snare wire is contracted, thereby preventing the snare wire from slipping off (for example, see Japanese Utility Model Application Post-Examination Publication No. 6-3549).

However, the structure in which a plurality of anti-slip tips are secured to the snare wire gives rise to another problem. That is, the process of manufacturing the snare becomes extremely complicated. In addition, the tips may catch on the distal end of the flexible sheath or another tip, making the wire loop difficult to expand or contract smoothly.

2. Field of the Invention

The present invention relates to a snare that is inserted into an instrument passage of an endoscope to excise a polyp.

BRIEF SUMMARY OF THE INVENTION

An object of the present invention is to provide a snare for an endoscope that is capable of readily and surely binding a polyp tight with a snare wire and easy to manufacture and that allows the snare wire to be expanded or contacted smoothly.

Other objects and advantages of the present invention will become apparent from the following detailed description of illustrated embodiments of the invention.

According to the present invention, there is provided a snare for an endoscope including a flexible sheath and a control wire axially movably inserted in the flexible sheath. A snare wire is connected to the distal end of the control wire. The snare wire is formed from an elastic wire. When the control wire is advanced axially, the snare wire projects from the distal end of the flexible sheath and expands in a loop shape by its own elasticity. When the control wire is retracted axially, the snare wire is pulled into the distal end of the flexible sheath and thus contracted. The distal end surface of the flexible sheath is provided with a plurality of claw-shaped projections projecting forward in parallel to each other.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
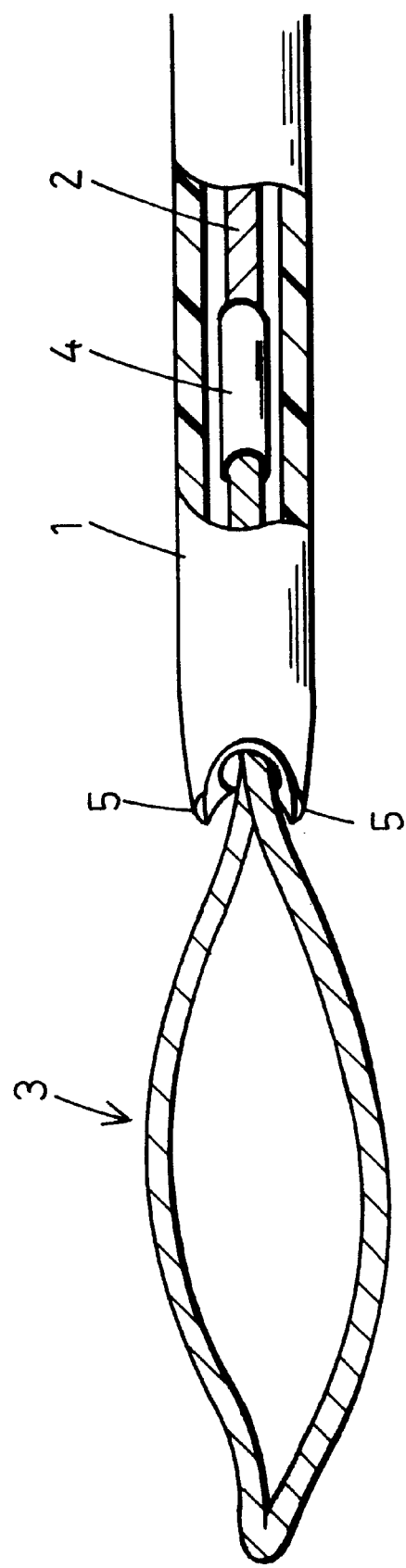
FIG. 1 is a partly-cutaway perspective view of a distal end portion of a snare for an endoscope according to a first embodiment of the present invention.

FIG. 1 shows a distal end portion of a snare for an endoscope according to a first embodiment of the present invention. A long, narrow tube-shaped flexible sheath 1 is formed from an electrically insulating tetrafluoroethylene resin tube, for example. The flexible sheath 1 is removably inserted into an instrument passage of an endoscope (not shown).

A control wire 2 made of a flexible electrically conductive metal is axially movably inserted in the flexible sheath 1 over the entire length thereof. The control wire 2 is advanced or retracted at a control part (not shown) connected to the proximal end of the flexible sheath 1.

A snare wire 3 formed from an electrically conductive elastic wire is connected to the distal end of the control wire 2 through a connecting pipe 4. It should be noted, however, that the snare wire 3 itself may be extended to form the control wire 2.

The snare wire 3 is formed from a single or stranded wire of a stainless steel, for example. Under conditions where no external force is applied thereto, the snare wire 3 forms a loop with a diameter of several centimeters as shown in FIG. 1. The snare wire 3 can be elastically deformed so as to contract by application of external force.

Accordingly, as the control wire 2 is actuated to advance or retract at the control part, the snare wire 3 projects from or withdraws into the distal end of the flexible sheath 1. When projecting from the distal end of the flexible sheath 1, the snare wire 3 expands in a loop shape by its own elasticity as shown in FIG. 1. When pulled into the distal end of the flexible sheath 1, the snare wire 3 contracts.

Although the snare wire 3 is formed by bending a single elastic wire in a U-shape, it may be formed by securing two elastic wires to each other at th e distal end portions thereof. If necessary, a tubular distal end tip may be provided on the secured end portions of the two elastic wires.

The flexible sheath 1 has a slightly tapered distal end portion. The central portion of the distal end of the flexible sheath 1 is cut laterally in a U-shape, thereby forming a pair of claw-shaped projections 5 projecting forward from 180-degree symmetric positions.

Figure 2:
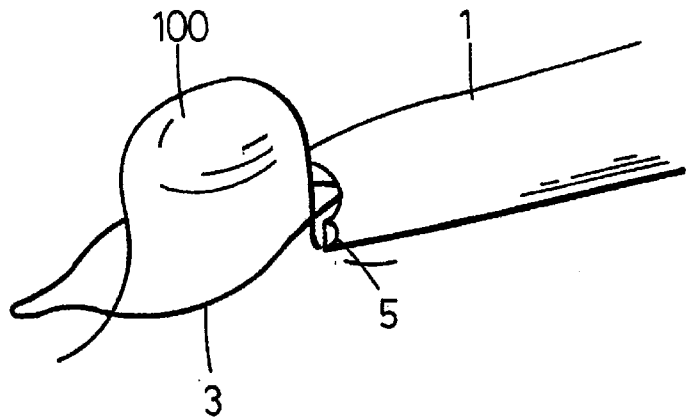
FIG. 2 is a schematic view illustrating a way of using the snare according to the first embodiment of the present invention.

Accordingly, when the pair of claw-shaped projections 5 are placed to hold a polyp 100 from both sides as shown in FIG. 2, as the flexible sheath 1 is pushed forward, the polyp 100 is caused to rise. Thus, the polyp 100 can be readily and surely bound tight with the snare wire 3.

Figure 3:
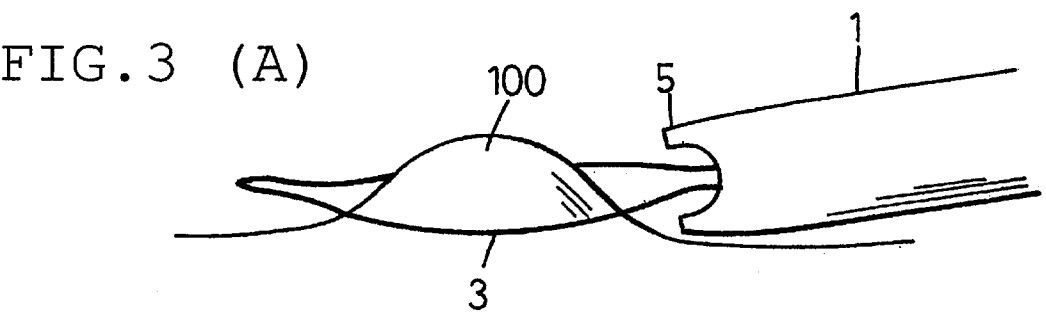
FIG. 3 is a schematic view illustrating a way of using the snare according to the first embodiment of the present invention, step by step.
Figure 3:
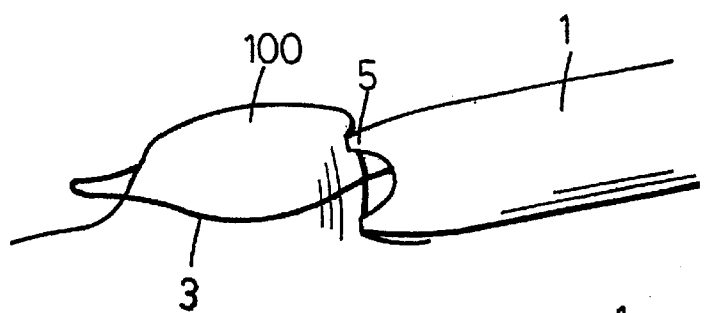
Figure 3:
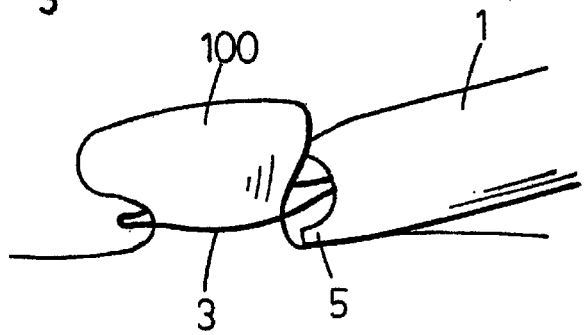

As shown in part (A) of FIG. 3, when the flexible sheath 1 faces a polyp 100 in such a way that an imaginary line connecting the pair of claw-shaped projections 5 extends parallel to an imaginary line connecting the top and base of the polyp 100, as the flexible sheath 1 is pushed forward, the claw-shaped projections 5 bite in to t he polyp 100 as shown in part (B) of FIG. 3. In this state, the snare wire 3 is pulled. Consequently, the polyp 100 can be readily and surely bound tight with the snare wire 3 as shown in part (C) of FIG. 3.

Figure 4:
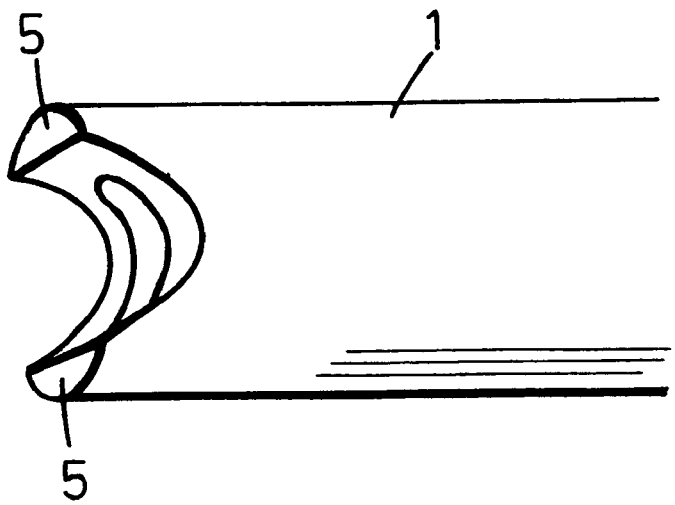
FIG. 4 is a perspective view showing claw-shaped projections of a snare for an endoscope according to a second embodiment of the present invention.
Figure 5:
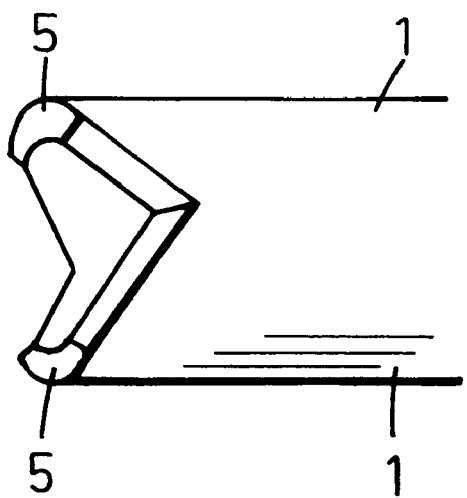
FIG. 5 is a perspective view showing claw-shaped projections of a snare for an endoscope according to a third embodiment of the present invention.
Figure 6:
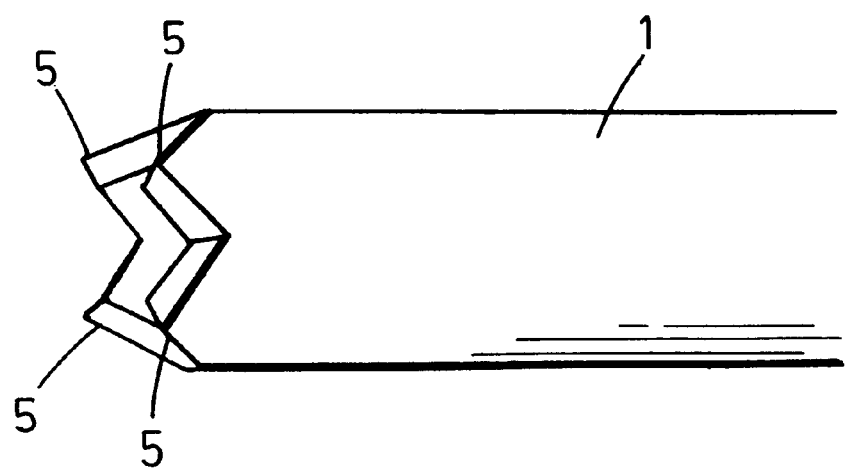
FIG. 6 is a perspective view showing claw-shaped projections of a snare for an endoscope according to a fourth embodiment of the present invention.

It should be noted that the present invention is not necessarily limited to the foregoing embodiment. Regarding the configuration of the claw-shaped projections 5, for example, the outer surfaces of the claw-shaped projections 5 need not be tapered, as shown in FIG. 4. The distal end of the flexible sheath 1 may be cut laterally in a V-shape as shown in FIG. 5. It is also possible to form three or more claw-shaped projections 5 as shown in FIG. 6 (four claw-shaped projections 5 are provided in FIG. 6). Alternatively, the claw-shaped projections 5 may be formed by a large number of serrations.

Figure 7:
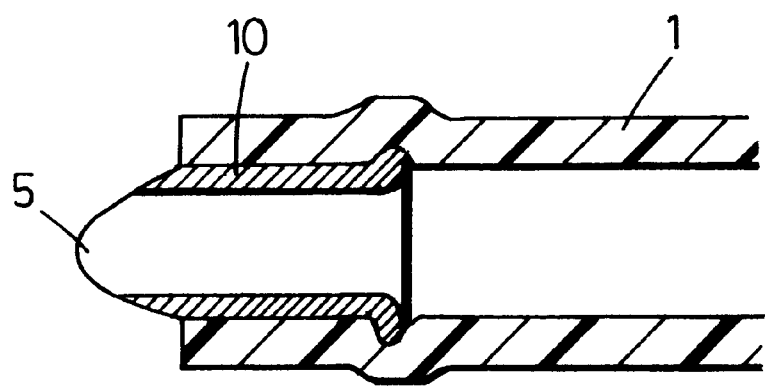
FIG. 7 is a perspective view showing claw-shaped projections of a snare for an endoscope according to a fifth embodiment of the present invention.

As shown in FIG. 7, a distal end tip 10 made, for example, of a metal or a rigid plastic material and formed with a plurality of claw-shaped projections 5 may be secured to the distal end of a flexible sheath 1 formed from a flexible tube.

According to the present invention, the distal end surface of the flexible sheath is formed with a plurality of claw-shaped projections projecting forward in parallel to each other. Thus, simply by pressing the flexible sheath against a polyp, the polyp can be readily and surely bound tight with the snare wire without slipping on the surface of the polyp. Moreover, the snare according to the present invention is extremely easy to manufacture. The claw-shaped projections have no adverse effect on the operation of expanding and contracting the snare wire.

While the invention has been described by reference to specific embodiments chosen for purposes of illustration, it should be apparent that numerous modifications could be made thereto by those skilled in the art without departing from the basic concept and scope of the invention.

What is claimed is:

1. A snare for an endoscope comprising:

a flexible sheath;

a control wire axially movably inserted in said flexible sheath; and a snare wire connected to a distal end of said control wire, said snare wire being formed from an elastic wire;

wherein when said control wire is advanced axially, said snare wire projects from a distal end of said flexible sheath and expands in a loop shape by its own elasticity, whereas when said control wire is retracted axially, said snare wire is pulled into the distal end of said flexible sheath and thus contracted;

wherein a distal end surface of said flexible sheath is provided with a plurality of claw-shaped projections projecting forward in parallel to each other.

2. A snare for an endoscope according to claim 1, wherein said flexible sheath is formed from a flexible tube, and said claw-shaped projections are formed on a distal end surface of said flexible tube.

3. A snare for an endoscope according to claim 1, wherein said flexible sheath is formed from a flexible tube, and a distal end tip formed with said claw-shaped projections is secured to a distal end of said flexible tube.

4. A snare for an endoscope according to claim 1, wherein said claw-shaped projections are a pair of claw-shaped projections formed in 180-degree symmetric relation to each other.

5. A snare for an endoscope according to claim 1, wherein said flexible sheath is formed in a tube shape, and said claw-shaped projections are formed by cutting a distal end portion of said flexible sheath into a U-shape or a V-shape as viewed from a side thereof.

6. A snare for an endoscope according to claim 1, wherein said claw-shaped projections are a plurality of serrations.

* * * * *